United States Patent
Ikuma et al.

(10) Patent No.: US 10,694,929 B2
(45) Date of Patent: Jun. 30, 2020

(54) MEDICAL EQUIPMENT SYSTEM AND OPERATION METHOD OF MEDICAL EQUIPMENT SYSTEM

(71) Applicant: OLYMPUS CORPORATION, Tokyo (JP)

(72) Inventors: Soichi Ikuma, Akishima (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 54 days.

(21) Appl. No.: 15/389,543

(22) Filed: Dec. 23, 2016

(65) Prior Publication Data
US 2017/0100019 A1    Apr. 13, 2017

Related U.S. Application Data

(63) Continuation of application No. PCT/JP2015/084551, filed on Dec. 9, 2015.

(30) Foreign Application Priority Data

Dec. 15, 2014 (JP) .................................. 2014-253276

(51) Int. Cl.
*A61B 1/04* (2006.01)
*A61B 5/06* (2006.01)
(Continued)

(52) U.S. Cl.
CPC .............. *A61B 1/04* (2013.01); *A61B 1/0002* (2013.01); *A61B 1/0005* (2013.01);
(Continued)

(58) Field of Classification Search
CPC ....... A61B 1/04; A61B 5/062; A61B 1/00045; A61B 1/00009; A61B 1/0002; A61B 1/0005; G02B 23/2484; G02B 21/367
See application file for complete search history.

(56) References Cited

U.S. PATENT DOCUMENTS

2005/0020878 A1    1/2005  Ohnishi et al.
2007/0142705 A1    6/2007  Ohnishi et al.
(Continued)

FOREIGN PATENT DOCUMENTS

EP      1466552 A1    10/2004
EP      1865458 A1    12/2007
(Continued)

OTHER PUBLICATIONS

International Search Report dated Feb. 16, 2016 issued in PCT/JP2015/084551.

*Primary Examiner* — Michael J Carey
(74) *Attorney, Agent, or Firm* — Scully, Scott, Murphy & Presser, P.C.

(57) ABSTRACT

A medical equipment system includes an image pickup information storage unit configured to store images and image pickup position information by associating the images and the image pickup position information with each other; a unit configured to calculate an image pickup position in 3D information on a luminal organ during image acquisition; a control unit configured to calculate a current image pickup position or image pickup area of the image pickup system in the 3D information; and an image processing unit configured to acquire images at image pickup positions overlapping the current image pickup position or image pickup area from storage results of the image pickup information storage unit and arrange the images based on a predetermined criterion on a region by region basis.

7 Claims, 9 Drawing Sheets

(51) Int. Cl.
  *A61B 1/00* (2006.01)
  *G02B 23/24* (2006.01)
  *G02B 21/36* (2006.01)

(52) U.S. Cl.
  CPC ...... *A61B 1/00009* (2013.01); *A61B 1/00045* (2013.01); *A61B 5/062* (2013.01); *G02B 23/2484* (2013.01); *G02B 21/367* (2013.01)

(56) References Cited

U.S. PATENT DOCUMENTS

| | | | |
|---|---|---|---|
| 2008/0039707 A1 | 2/2008 | Sugiyama et al. | |
| 2012/0027260 A1* | 2/2012 | Truyen | A61B 1/0005 382/103 |
| 2013/0152020 A1* | 6/2013 | Nishiyama | A61B 1/00009 715/835 |
| 2014/0088357 A1 | 3/2014 | Ikuma et al. | |
| 2015/0015612 A1* | 1/2015 | Kurosaki | G06F 19/321 345/636 |
| 2016/0000307 A1* | 1/2016 | Akimoto | A61B 1/04 600/109 |

FOREIGN PATENT DOCUMENTS

| | | |
|---|---|---|
| EP | 2601880 A1 | 6/2013 |
| EP | 2700351 A1 | 2/2014 |
| JP | 2002-017751 A | 1/2002 |
| JP | 4009639 B2 | 11/2007 |
| JP | 2007-325742 A | 12/2007 |
| JP | 2013-085593 A | 5/2013 |
| JP | 5197892 B2 | 5/2013 |
| JP | 5378628 B1 | 12/2013 |
| JP | 5771757 B2 | 7/2015 |
| WO | WO 2004/010857 A1 | 2/2004 |
| WO | WO 2012/132840 A1 | 10/2012 |
| WO | WO 2013/132880 A1 | 9/2013 |
| WO | WO 2014/168128 A1 | 10/2014 |

* cited by examiner

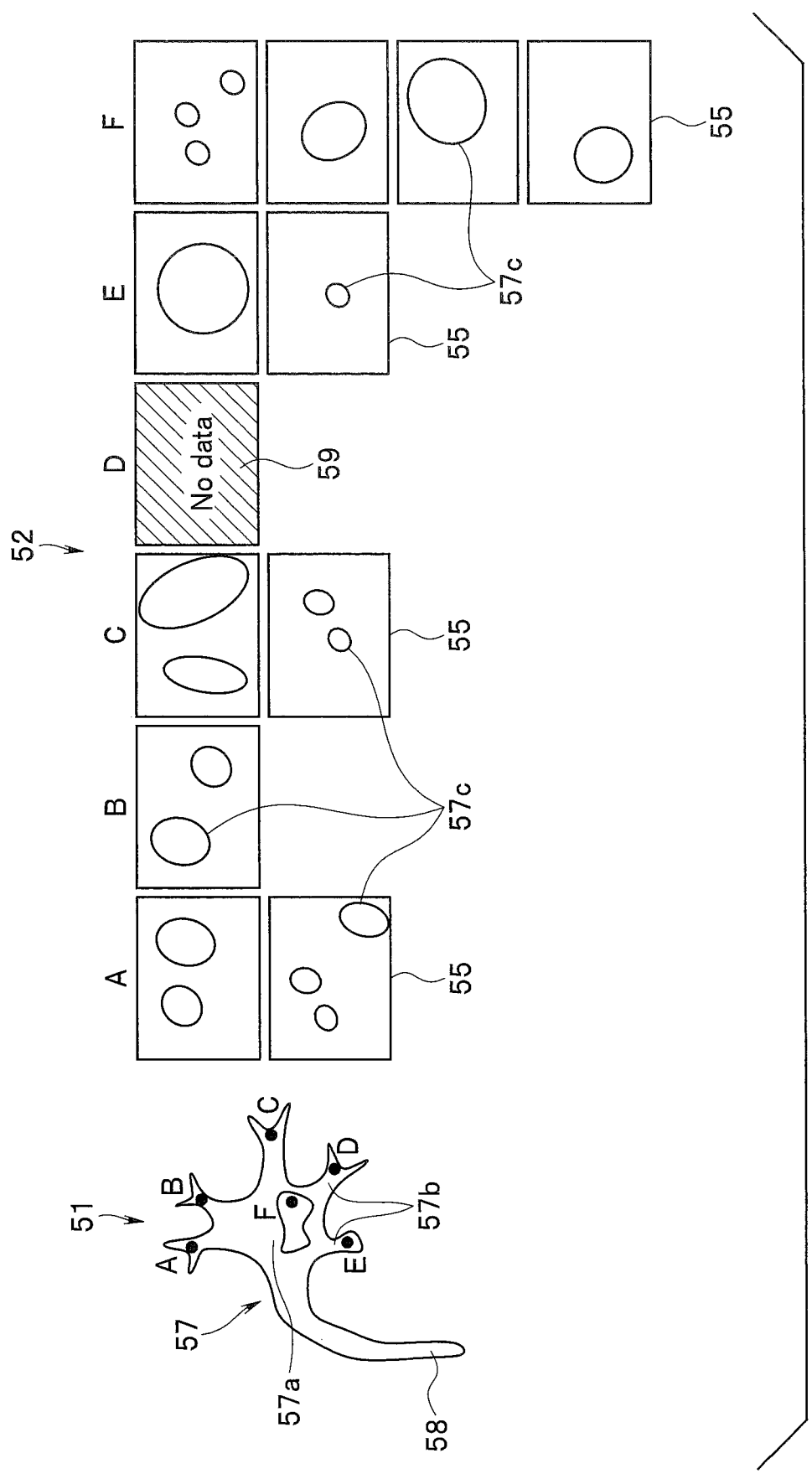

MEDICAL EQUIPMENT SYSTEM AND OPERATION METHOD OF MEDICAL EQUIPMENT SYSTEM

CROSS REFERENCE TO RELATED APPLICATION

This application is a continuation application of PCT/JP2015/084551 filed on Dec. 9, 2015 and claims benefit of Japanese Application No. 2014-253276 filed in Japan on Dec. 15, 2014, the entire contents of which are incorporated herein by this reference.

BACKGROUND OF THE INVENTION

1. Field of the Invention

The present invention relates to a medical equipment system configured to pick up object images in a luminal organ and thereby acquire and display picked-up images as well as to an operation method of the medical equipment system.

2. Description of the Related Art

Regarding the medical equipment system configured to pick up object images in a luminal organ and thereby acquire and display picked-up images, various such systems have been proposed conventionally.

For example, FIG. 12 and the like of Japanese Patent No. 4009639 describe how VBS images at all branch points on a route are reduced and displayed as branch thumbnail VBS images while displaying live images and VBS images of a bronchus on a navigation screen. Here, the VBS images are virtual endoscopic images of a body cavity tract in a subject, generated based on CT image data, which is image data on a three-dimensional region of the subject.

Also, Japanese Patent Application Laid-Open Publication No. 2002-17751 describes a technique for calculating a distance between a distal end of a rigid endoscope and a target site of the subject and displaying a magnified view of a three-directional projected image of a head portion shown in FIG. 10 in such a way as shown in FIG. 11 when the distal end of the rigid endoscope comes closer to the target site than a predetermined distance.

Incidentally, in observing a luminal organ with an endoscope, plural picked-up images of an observed object (e.g., a tumor) in the luminal organ may sometimes be acquired from different directions. As a method for displaying and checking plural picked-up images acquired in this way, a method for displaying the images in time series has been known conventionally.

SUMMARY OF THE INVENTION

A medical equipment system according to one aspect of the present invention includes, an image pickup information storage unit configured to store a picked-up image obtained by picking up an object image in a predetermined luminal organ and image pickup position information on a position at which the object image is picked up, by associating the picked-up image and the image pickup position information with each other; an objective optical window configured to form the object image in the predetermined luminal organ; an image pickup unit configured to pick up the object image and thereby acquire the picked-up image; a position information acquisition unit configured to acquire position information on the objective optical window; an alignment unit configured to align the position information acquired by the position information acquisition unit with three-dimensional shape information on the predetermined luminal organ; an image pickup position calculation unit configured to align the position information with the three-dimensional shape information using the alignment unit upon acquisition of the picked-up image by the image pickup unit and calculate image pickup position information on a position at which the picked-up image in the three-dimensional shape information is acquired; a control unit configured to calculate a current image pickup position or image pickup area of the image pickup unit, in the three-dimensional shape information, based on the position information acquired by the position information acquisition unit; and an image processing unit configured to identify the image pickup position information at least partially overlapping the current image pickup position or image pickup area of the image pickup unit, calculated by the control unit, based on storage results of the image pickup information storage unit, acquire the picked-up image associated with the identified image pickup position information from the image pickup information storage unit, and generate an image string by arranging the acquired picked-up image based on a predetermined criterion.

An operation method of a medical equipment system according to one aspect of the present invention includes, a step in which an image pickup information storage unit stores a picked-up image obtained by picking up an object image in a predetermined luminal organ and image pickup position information on a position at which the object image is picked up, by associating the picked-up image and the image pickup position information with each other; a step in which an objective optical window forms the object image in the predetermined luminal organ; a step in which an image pickup unit picks up the object image and thereby acquires the picked-up image; a step in which a position information acquisition unit acquires position information on the objective optical window; a step in which an alignment unit aligns the position information acquired by the position information acquisition unit with three-dimensional shape information on the predetermined luminal organ; a step in which an image pickup position calculation unit aligns the position information with the three-dimensional shape information using the alignment unit upon acquisition of the picked-up image by the image pickup unit and calculates image pickup position information on a position at which the picked-up image in the three-dimensional shape information is acquired; a step in which a control unit calculates a current image pickup position or image pickup area of the image pickup unit, in the three-dimensional shape information, based on the position information acquired by the position information acquisition unit; and a step in which an image processing unit identifies the image pickup position information at least partially overlapping the current image pickup position or image pickup area of the image pickup unit, calculated by the control unit, based on storage results of the image pickup information storage unit, acquires the picked-up image associated with the identified image pickup position information from the image pickup information storage unit, and generates an image string by arranging the acquired picked-up image based on a predetermined criterion.

BRIEF DESCRIPTION OF THE DRAWINGS

FIG. 11 is a diagram showing an example in which picked-up images for each specified position or region are displayed together with a map on a monitor in the medical equipment system according to the second embodiment.

DETAILED DESCRIPTION OF THE PREFERRED EMBODIMENT(S)

Embodiments of the present invention will be described below with reference to the drawings.

First Embodiment

Figure 1:
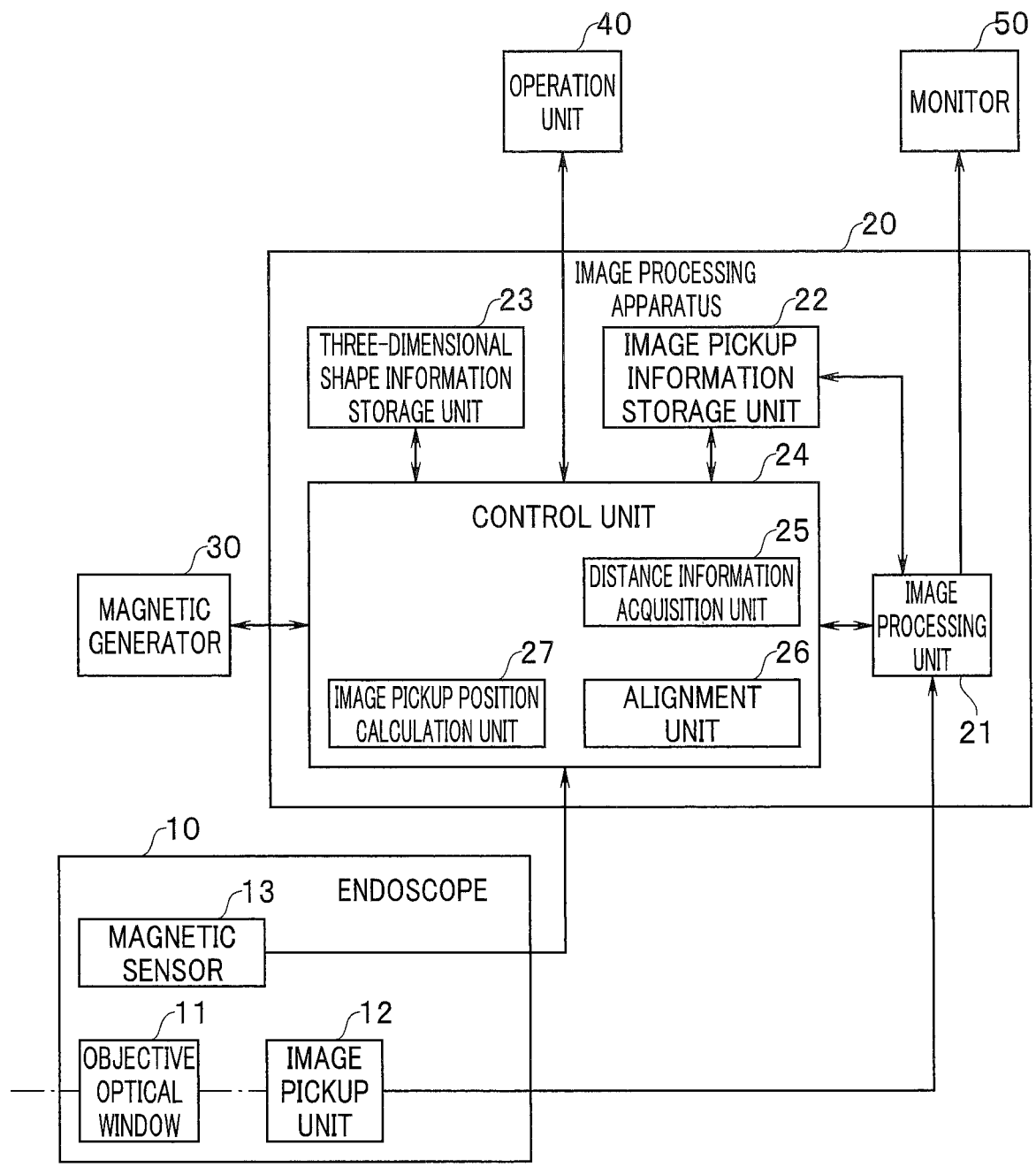
FIG. 1 is a block diagram showing a configuration of a medical equipment system according to a first embodiment of the present invention.

FIGS. 1 to 7 show a first embodiment of the present invention, where FIG. 1 is a block diagram showing a configuration of a medical equipment system.

The medical equipment system includes an endoscope 10, an image processing apparatus 20, a magnetic generator 30, an operation unit 40, and a monitor 50.

The magnetic generator 30 is designed to generate a magnetic field for position detection under control of an under-mentioned control unit 24 in the image processing apparatus 20.

The operation unit 40 is used to enter various operation inputs to the image processing apparatus 20 (and thus the medical equipment system) and includes devices such as a touch panel, a keyboard, a mouse, a track ball, and a foot switch as appropriate. The operation unit 40 functions as a specification unit used to manually specify a predetermined position or region in three-dimensional shape information described later (a specification unit for automatic specification corresponds to the control unit 24 and the like described later). Also, the operation unit 40 is also used for a selection operation with respect to a three-dimensional model image described later.

The monitor 50 is a display apparatus configured to display picked-up images 55 acquired from the endoscope 10 (see FIG. 3 and the like), a map 51 (see FIG. 3 and the like) of a predetermined luminal organ generated by the image processing apparatus 20 based on three-dimensional shape information, various settings information on the medical equipment system, and the like.

The endoscope 10 includes an objective optical window 11, an image pickup unit 12, and a magnetic sensor 13. Here, the endoscope 10 may be designed for use in white light observation in normal white light or may be designed to be capable of special light observation in special light such as NBI (narrow band imaging) light in addition to, or instead of, white light observation. Special light observation in an appropriate special light provides the advantage of making it easy to discover a tumor or the like.

The objective optical window 11 includes, for example, optical members such as lenses and forms an object image (optical image of an object) in a predetermined luminal organ on the image pickup unit 12. Note that the predetermined luminal organ is assumed to be, for example, the bladder 56 in the description of the present embodiment (see FIG. 3 and FIGS. 5 to 7), but may be, of course, another luminal organ (an example of other luminal organs (renal pelvis and renal calyxes) is shown in a second embodiment described later).

The image pickup unit 12 picks up the object image formed by the objective optical window 11 and thereby acquires a picked-up image 55. The image pickup unit 12 is provided in the endoscope 10 in the example shown in FIG. 1, but when the endoscope 10 is an optical endoscope equipped with a relay optical system or the like, the image pickup unit 12 may be a camera head or the like used by being attached to an eyepiece of the optical endoscope.

The magnetic sensor 13 is a position information acquisition unit, configured to acquire position information on the objective optical window 11 by detecting a magnetic field generated by the magnetic generator 30. Note that although the magnetic sensor 13 is used here as the position information acquisition unit, another techniques may be used alternatively.

The image processing apparatus 20 includes an image processing unit 21, an image pickup information storage unit 22, a three-dimensional shape information storage unit 23, and a control unit 24. The control unit 24 includes a distance information acquisition unit 25, an alignment unit 26, and an image pickup position calculation unit 27.

First, the control unit 24 controls the entire medical equipment system, including various parts of the image processing apparatus 20.

The three-dimensional shape information storage unit 23 stores three-dimensional shape information on the predetermined luminal organ. Here, the three-dimensional shape information is, for example, a three-dimensional model image of the luminal organ, three-dimensional image information on the luminal organ acquired from the subject himself/herself, or the like, and is assumed to be a three-dimensional model image of the luminal organ in the present embodiment. However, the luminal organ may vary in size and shape depending on age, sex, or the like. Thus, when a three-dimensional model image is used as the three-dimensional shape information, it is advisable to store plural three-dimensional model images differing in size and shape in the three-dimensional shape information storage unit 23 beforehand, allowing a desired three-dimensional model image to be selected through a selection operation performed on the operation unit 40.

The alignment unit 26 aligns position information acquired by the magnetic sensor 13 with three-dimensional shape information. That is, the alignment unit 26 calculates to what position in the three-dimensional shape information read out of the three-dimensional shape information storage unit 23 the position of the objective optical window 11 corresponds when the endoscope 10 is inserted in the predetermined luminal organ.

The distance information acquisition unit 25 acquires distance information on a distance from the objective optical window 11 to the predetermined luminal organ. The distance information acquisition unit 25 may acquire the distance information using, for example, 3D ranging, laser ranging, or another appropriate ranging technique without being limited to any specific technique.

Upon acquisition of the picked-up image 55 by the image pickup unit 12, the image pickup position calculation unit 27 aligns the position information on the objective optical window 11 at a time of the acquisition of the picked-up image 55 with the three-dimensional shape information using the alignment unit 26. Then, based on the aligned position information and the distance information acquired from the distance information acquisition unit 25, the image pickup position calculation unit 27 calculates an image pickup area (i.e., an area of the predetermined luminal organ shown in the picked-up image 55 in the three-dimensional shape information) in the predetermined luminal organ in the three-dimensional shape information on the picked-up image 55 as image pickup position information in the three-dimensional shape information.

The image processing unit 21 performs various image processing such as a white balance process, a synchronization process, and gamma conversion on the picked-up image 55 acquired from the image pickup unit 12 and outputs and stores the image in the image pickup information storage unit 22.

Under the control of the control unit 24, the image pickup information storage unit 22 stores the image pickup position information calculated by the image pickup position calculation unit 27 and the picked-up image 55 subjected to image processing by the image processing unit 21 by associating the image pickup position information and picked-up image 55 with each other. Note that the information stored by the image pickup information storage unit 22 by being associated with the picked-up image 55 may include some other information such as a predetermined criterion described later in addition to the image pickup position information.

Furthermore, based on the three-dimensional shape information read out of the three-dimensional shape information storage unit 23, the image processing unit 21 described above generates a map 51 of the predetermined luminal organ and outputs the map 51 to the monitor 50 in order for the map 51 to be displayed. With reference to the map 51 displayed on the monitor 50, a user specifies a predetermined position or region in the three-dimensional shape information using the operation unit 40 described above.

Then, the image processing unit 21 identifies all the image pickup position information at least partially overlapping the position or region specified via the operation unit 40 or by the control unit 24, based on storage results of the image pickup information storage unit 22, acquires all the picked-up images 55 associated with the identified image pickup position information from the image pickup information storage unit 22, and generates an image string 52 (see FIGS. 3, 7, and the like) by arranging the acquired picked-up images 55 for each position or region based on a predetermined criterion.

Here, examples of the predetermined criterion include, but are not limited to, distance information acquired by the distance information acquisition unit 25 concerning a distance from the objective optical window 11 to the image pickup position (e.g., a center of an area picked up of an object (the object is a test object for the endoscope 10, and thus is sometimes referred to also as a subject as appropriate)), a distance from a specific position (e.g., a center (current image pickup position) of a current image pickup area (current observation field of view), or a specified position, a center of a specified region, or a specific site (e.g., the urethral opening 56a in the bladder 56) of the subject, etc.) of the subject to a position indicated by the image pickup position information, a time series representing a time-sequential order in which the picked-up images 55 are acquired, and a size of a predetermined feature site (such as a tumor) in the predetermined luminal organ. Then, the acquired predetermined criterion is stored in the image pickup information storage unit 22 by being associated with the picked-up images 55 described above.

Also, the image processing unit 21 is configured to be able to selectively change the predetermined criterion used in arranging the picked-up images 55 among the plural criteria. Here, the predetermined criterion may be either selected automatically by the control unit 24 according to the predetermined luminal organ or the like to be examined or selected manually by the user via the operation unit 40.

Figure 2:
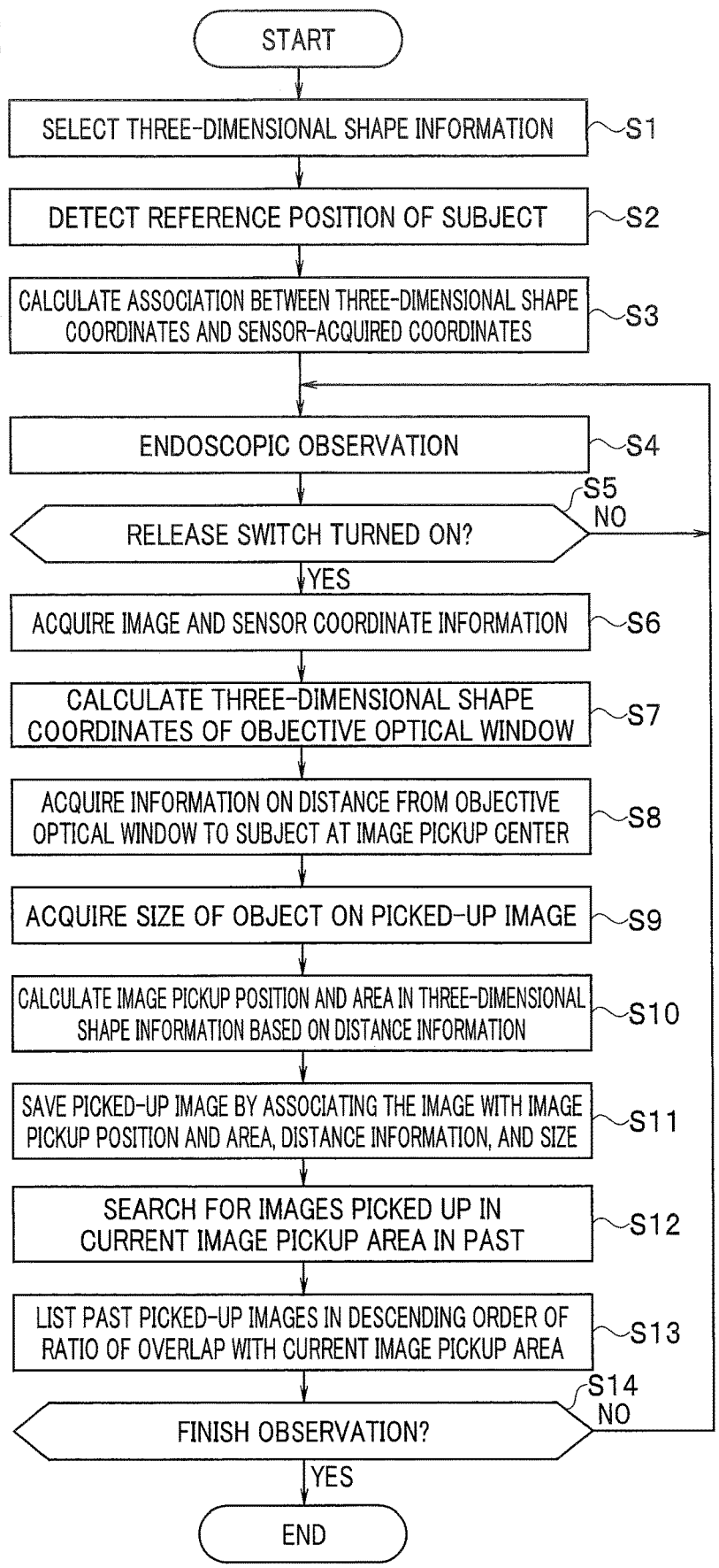
FIG. 2 is a flowchart showing a process of observing an object using a medical equipment system according to the first embodiment.

Next, FIG. 2 is a flowchart showing a process of observing an object using the medical equipment system according to the first embodiment.

Once the process is started, a three-dimensional model image of the predetermined luminal organ, i.e., for example, the bladder 56, which provides three-dimensional shape information here, is selected from plural three-dimensional model images such as described above and read out of three-dimensional shape information storage unit 23 (Step S1).

Next, an insertion portion of the endoscope 10 is inserted into the subject, and with a distal end of the insertion portion being placed in contact with a reference position of the subject, such as the urethral opening 56a (see FIG. 3 and FIGS. 5 to 7), which is a boundary between the bladder 56 and urethra, position detection is done using the magnetic sensor 13, thereby detecting the reference position of the subject (Step S2).

Then, association between position information (sensor coordinate information) detected by the magnetic sensor 13 and coordinates (three-dimensional shape coordinates) in the three-dimensional shape information is calculated by the alignment unit 26 (Step S3). Note that although an example in which sensor coordinate information on the reference position (urethral opening 56a) acquired in Step S2 is associated with three-dimensional shape coordinates has been shown here (concrete examples of association include calculation of a transformation law between sensor coordinate information and three-dimensional shape coordinates), this is not restrictive, and another appropriate technique can be used. Once the association is calculated, position information detected by the magnetic sensor 13 at any time point can subsequently be aligned with three-dimensional shape information.

Then, observations (i.e., observations carried out by acquiring a real-time movie with the image pickup unit 12 and displaying the real-time movie on the monitor 50) in the luminal organ are carried out with the endoscope 10 using the white light observation or special light observation described above (Step S4). If a tumor is discovered during observation, the user inputs the discovery of the tumor to the medical equipment system by turning on a release switch. To respond to this, the control unit 24 judges whether or not the release switch is turned on (Step S5). The release switch here corresponds, for example, to a foot switch of the operation unit 40 or a non-illustrated scope switch provided on the endoscope 10.

If it is judged that the release switch is not turned on, the control unit 24 returns to Step S4 to continue endoscopic observation.

On the other hand, if it is judged in Step S5 that the release switch is turned on, the image pickup unit 12 acquires the picked-up image 55 as a still image and acquires sensor coordinate information at a time point when the release switch is turned on from the magnetic sensor 13 (Step S6).

The sensor coordinate information acquired here can be treated as approximate tumor position information, but it is more advisable to calculate more accurate tumor position information using the sensor coordinate information and distance information acquired in Step S8 described later.

Then, based on the acquired sensor coordinate information and the association calculated in Step S3, the alignment unit 26 calculates three-dimensional shape coordinates of the objective optical window 11 (Step S7).

Also, the distance information acquisition unit 25 acquires distance information on a distance from the objective optical window 11 to, for example, a center of the image pickup area in the subject when the release switch is turned on (Step S8).

Next, the image pickup position calculation unit 27 acquires size of an object (e.g., a predetermined feature site such as a tumor on the picked-up image 55) on the picked-up image 55 based on the acquired distance information (Step S9).

Note that although the size of an object (predetermined feature site) is calculated here based on distance information, but this is not restrictive. For example, while acquiring position information using the magnetic sensor 13, the user may trace a contour of an object with the distal end of the insertion portion of the endoscope 10 and the size of the object may be calculated based on a trajectory obtained by the tracing. Alternatively, another appropriate technique may be used.

Also, although the process of Step S9 is performed here by assuming that the size of the object (predetermined feature site) is used as the predetermined criterion in arranging and displaying images, the process of Step S9 may be omitted if the predetermined criterion is not used.

Based on the three-dimensional shape coordinates of the objective optical window 11 calculated in Step S7, the distance information acquired in Step S8, and angle-of-view information on the endoscope 10 (the angle-of-view information is acquired from the endoscope 10 by the control unit 24, for example, when the endoscope 10 gets connected to the image processing apparatus 20), at least one of (e.g., both, in this case) the image pickup area in the three-dimensional shape information on the picked-up image 55 acquired in Step S6 (i.e., image pickup area on an inner wall surface of the predetermined luminal organ, provided as three-dimensional shape information), and an image pickup position, which is, for example, a center of the image pickup area is calculated (Step S10).

Then, the picked-up image 55 subjected to image processing by the image processing unit 21, the image pickup position and image pickup area calculated by the image pickup position calculation unit 27, the distance information acquired by the distance information acquisition unit 25, and size information on the object (predetermined feature site) acquired in Step S9 are saved in the image pickup information storage unit 22 by being associated with one another (Step S11).

Note that although image pickup position, image pickup area, distance information, and size information on the object (predetermined feature site) have been cited as examples of the information stored by being associated with the picked-up image 55, some pieces of the information may be omitted or other piece of information (e.g., the above-mentioned distance from a specific position of the subject to a position indicated by the image pickup position information) may be stored by being associated with the picked-up image 55 in addition to the cited information or instead of any of the cited information.

Also, when saved in the image pickup information storage unit 22, the picked-up image 55 is generally saved, for example, in an image file or other file format and time information such as image pickup time or file storage time is recorded in the image file. Thus, it goes without saying that such time information is included in the information stored by being associated with the picked-up image 55.

Based on the position information obtained from the magnetic sensor 13, the control unit 24 calculates and specifies the current image pickup position or image pickup area (thus, the control unit 24 functions as a specification unit configured to automatically specify a predetermined position or region in three-dimensional shape information), and searches the picked-up images 55 stored in the image pickup information storage unit 22 for any image (e.g., picked-up image 55 of which the image pickup area at least partially overlaps the current image pickup position or image pickup area) picked up in the past at the current image pickup position (e.g., the center of the current image pickup area) or in the current image pickup area (Step S12).

Figure 3:
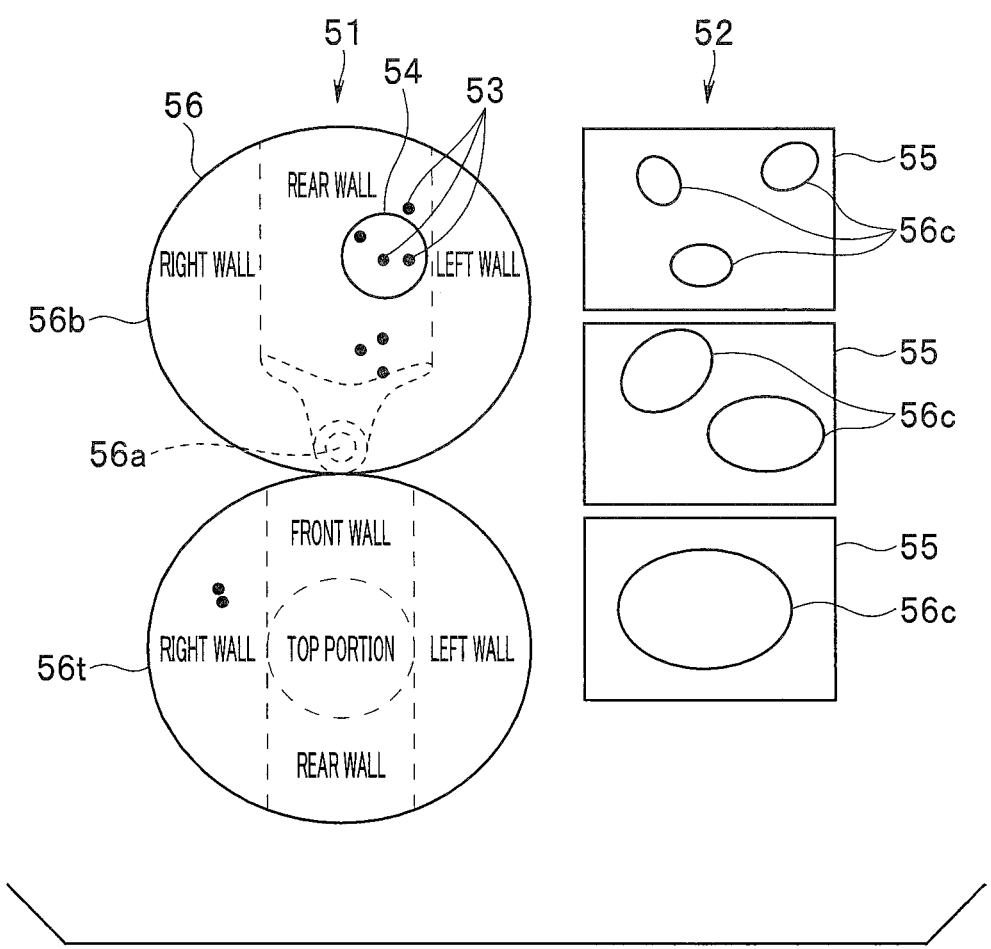
FIG. 3 is a diagram showing an example of images displayed on a monitor during endoscopic observation in the medical equipment system according to the first embodiment.

Then, the control unit 24 presents a display such as shown in FIG. 3 (Step S13). FIG. 3 is a diagram showing an example of images displayed on the monitor 50 in the medical equipment system during endoscopic observation.

As illustrated, a map 51 of the predetermined luminal organ created from three-dimensional shape information and an image string 52 are displayed, for example, next to each other on right and left on the monitor 50.

In the example shown in FIG. 3, a lower hemisphere map 56b and upper hemisphere map 56t, which are a two-dimensional development diagram of an inner wall of the bladder 56, which is the predetermined luminal organ, are displayed as the map 51. The urethral opening 56a used as a reference position in Step S2 is further displayed in the two-dimensional development diagram of the bladder 56.

The control unit 24 further displays a past image pickup position 53 and the current image pickup position or image pickup area (in the example shown in FIG. 3, a current image pickup area 54, which is a specified predetermined region) on the map 51.

Then, as the image string 52, the control unit 24 selects past picked-up images 55 of which the image pickup positions 53 at least partially overlap the current image pickup area 54, based on any of the predetermined criteria described above and lists the past picked-up images 55 next to one another (in the example shown in FIG. 3, three picked-up images 55 are displayed by being arranged in a vertical direction).

In Step S13, for example, a distance from a specific site of the subject to the image pickup position is used as the predetermined criterion, the specific site is set to the current image pickup position, and the picked-up images 55 are listed in order of increasing distance of image pickup position from the current image pickup position (the center of the current observation field of view). In this case, the past picked-up images 55 are listed in descending order of ratio of overlap with the current image pickup area 54. The listed picked-up images 55 are those picked up by the user in Step S5 by operating the release switch upon discovery of a tumor 56c, and thus the picked-up images 55 show the tumor 56c.

Since the past picked-up images 55 in the current image pickup area 54 are displayed by being arranged in this way, the user can determine promptly and appropriately whether to further acquire images in the current image pickup area 54, or to move the image pickup area, or to finish the observation.

Specifically, in the example shown in FIG. 3, the image string 52 includes picked-up images 55 (top and center picked-up images) showing a general bird's-eye view of plural tumors 56c and a picked-up image 55 (bottom picked-up image 55) showing a close frontal view of only one of the plural tumors 56c.

Thus, based on features displayed on the picked-up images 55 of the image string 52, the user can, for example, determine to acquire close-up images of other tumors 56c not photographed at close range. In this way, in relation to the tumors 56c, the user can determine to further acquire a close-up image, acquire a more enlarged image, acquire an image from a different direction, further or acquire a bird's-eye image when no bird's-eye image is contained, reacquire an image when there is blur, or reacquire an image by changing a light source from white light to special light, and so on.

Then, the control unit 24 judges whether or not to finish the observation (Step S14). When it is judged that the observation is not to be finished, the control unit 24 returns to Step S4 to continue the endoscopic observation, but when it is judged that the observation is to be finished, the control unit 24 finishes the process.

Figure 4:
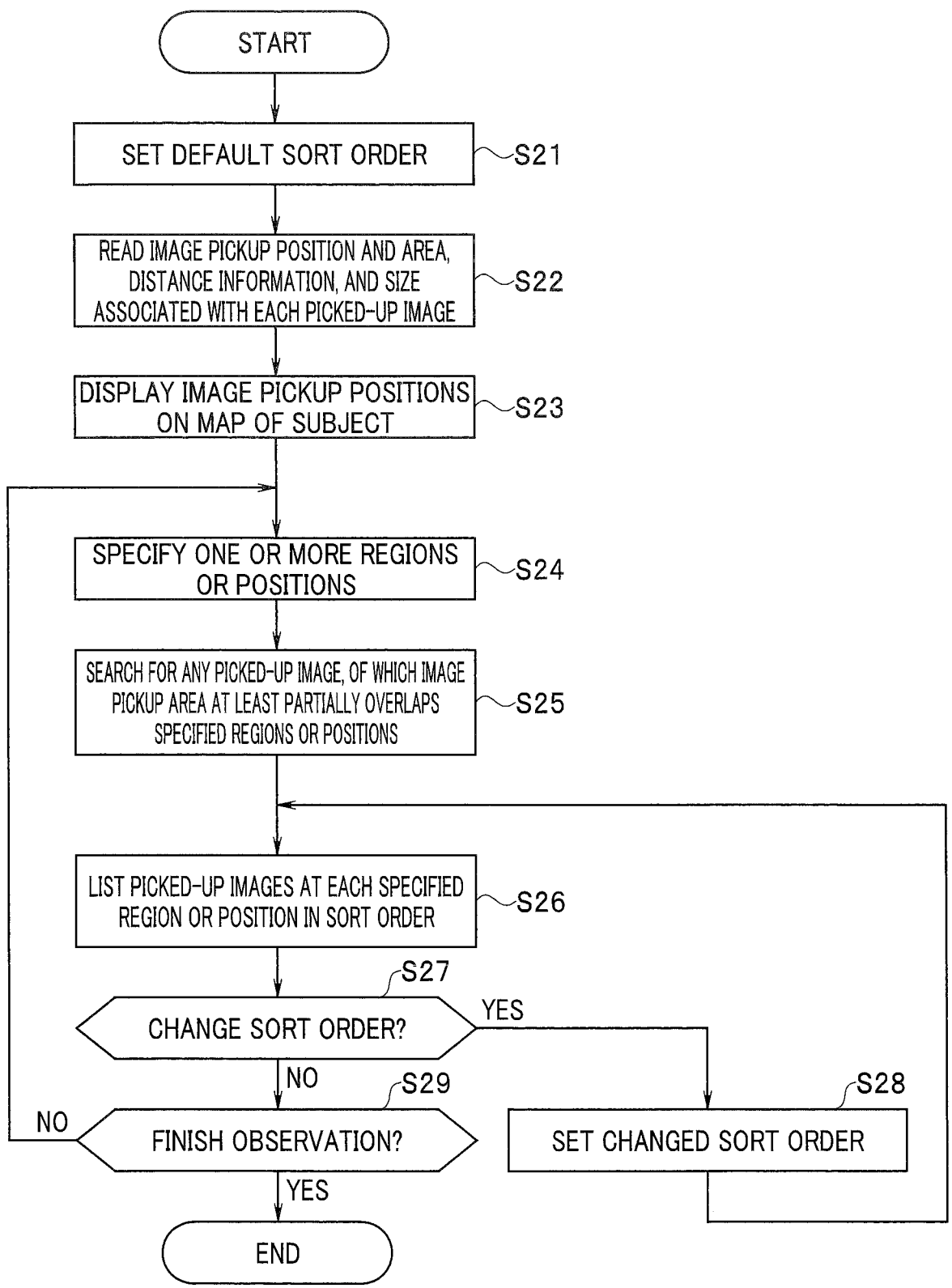
FIG. 4 is a flowchart of a process of reviewing an image to carry out diagnosis and the like in the medical equipment system according to the first embodiment after observation with an endoscope is finished.

Next, FIG. 4 is a flowchart of a process of reviewing an image to carry out diagnosis and the like in the medical equipment system after observation with the endoscope 10 is finished.

Once the process is started, the control unit 24 sets a default sort order (list order) for the image string 52 (Step S21). Here, the default sort order is a sort order set as a basis on the medical equipment system, a sort order used the last time, or the like. The sort order is set according to a predetermined criterion, such as described above, for arranging and displaying images.

Next, the control unit 24 reads the image pickup position, image pickup area, distance information, size information, and the like associated with each picked-up image 55 (Step S22).

Figure 5:
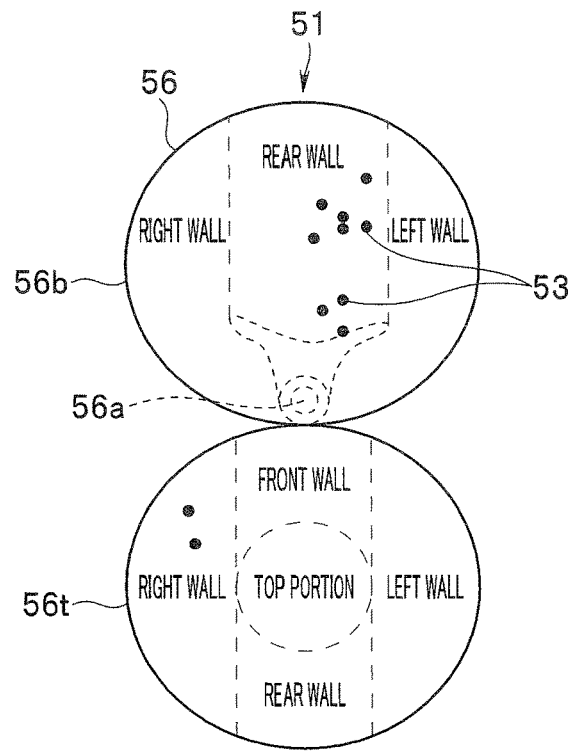
FIG. 5 is a diagram showing a display example of a map presented before a position or region is specified in the medical equipment system according to the first embodiment.

Then, as shown in FIG. 5, the map 51 of the predetermined luminal organ is displayed on the monitor 50 by being created from three-dimensional shape information on the subject, and furthermore, the image pickup positions 53 of the respective picked-up images 55 stored in the image pickup information storage unit 22 are displayed on the map 51 (Step S23).

Here, FIG. 5 is a diagram showing a display example of a map 51 presented before a position or region is specified in the medical equipment system. As with the example shown in FIG. 3, the map 51 shown in FIG. 5 is a two-dimensional development diagram of an inner wall of the bladder 56, and displays a lower hemisphere map 56b, an upper hemisphere map 56t, and the urethral opening 56a.

Subsequently, the user viewing a monitor display in FIG. 5 specifies a position or region in which the user wants to select a diagnostic image, using the mouse, track ball, or the like on the operation unit 40, which is a specification unit (Step S24). Here, when the process of Step S24 is performed first, one or more desired positions or regions are specified. In the second and subsequent times, if a position or region is not specified additionally (or newly by canceling the existing ones), the control unit 24 goes to a next process based on the position or region already specified.

Figure 6:
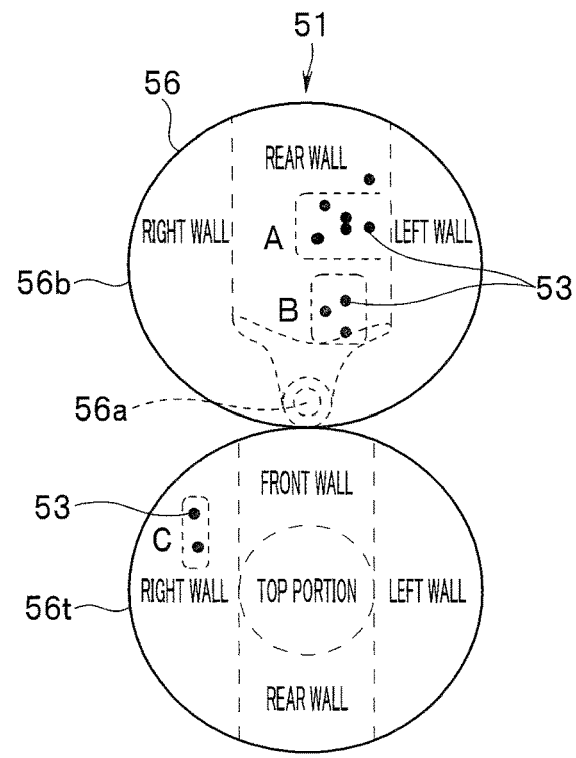
FIG. 6 is a diagram showing an example of a display presented after a position or region is specified on a map in the medical equipment system according to the first embodiment.

FIG. 6 is a diagram showing an example of a display presented after a position or region is specified on the map 51 in the medical equipment system. In the example shown in FIG. 6, regions A, B, and C including one or more image pickup positions 53 have been specified, but positions (points) may be specified instead of the regions.

Then, the control unit 24 searches the picked-up images 55 stored in the image pickup information storage unit 22 for any picked-up image 55 of which the image pickup area at least partially overlaps the specified positions or regions (Step S25).

Then, under the control of the control unit 24, the image processing unit 21 arranges the retrieved picked-up images 55 for each specified position or region in sort order, based on a predetermined criterion and lists the picked-up images 55 as an image string 52 next to the map 51 on the monitor 50 (Step S26).

Figure 7:
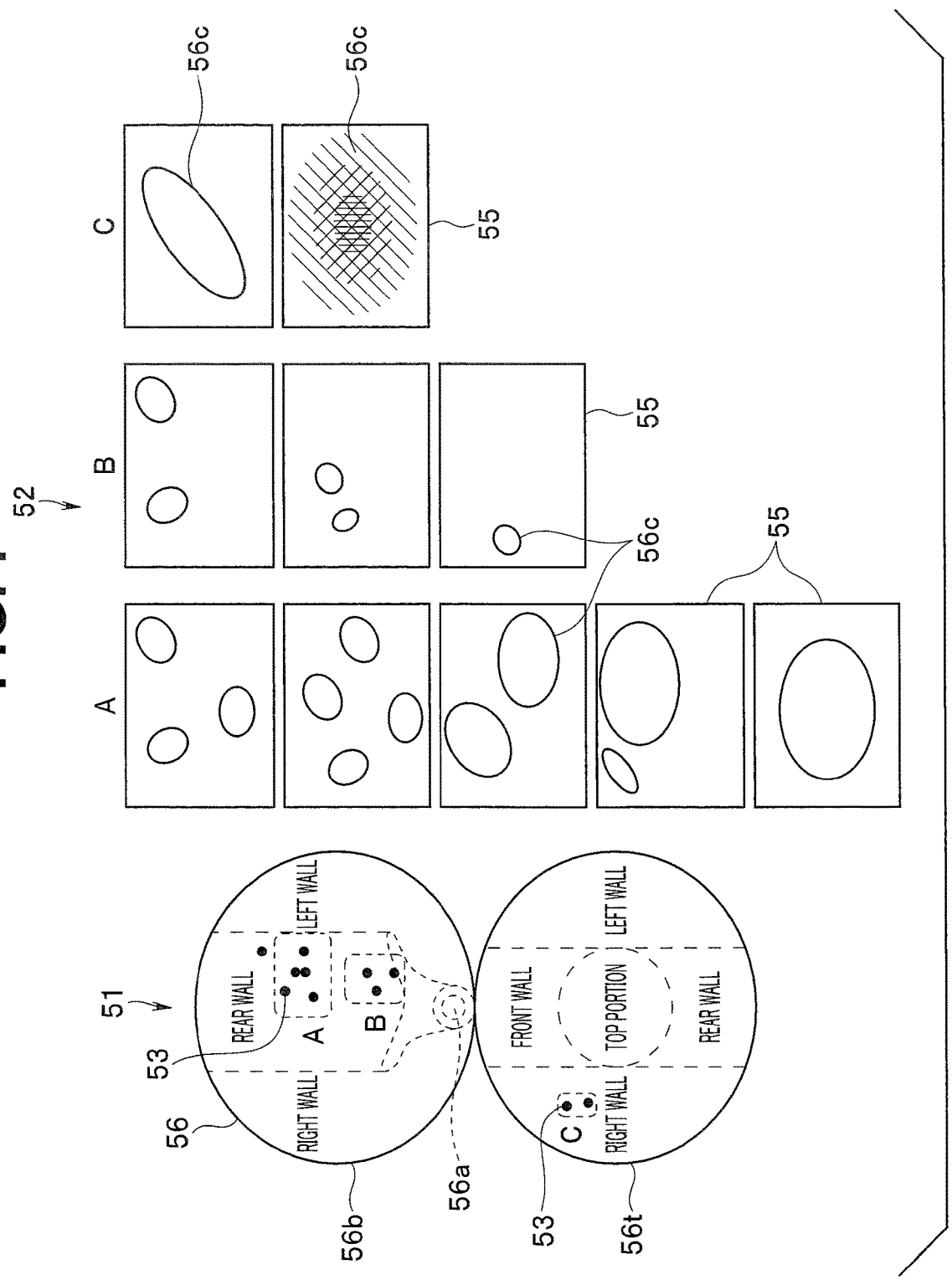
FIG. 7 is a diagram showing an example in which a map and image strings are displayed in the medical equipment system according to the first embodiment.

FIG. 7 is a diagram showing an example in which a map 51 and image strings 52 are displayed in the medical equipment system. In the example shown in FIG. 7, the picked-up images 55 of which the image pickup positions 53 overlap at least part of each of the regions A, B, and C are displayed by being arranged in the vertical direction.

In the example shown in FIG. 7, the user can make determinations and selections such as described below based on features displayed on the picked-up images 55 belonging to each of the regions A, B, and C.

First, the image string 52 of the region A includes picked-up images 55 showing a bird's-eye view of plural tumors 56c (top first to fourth picked-up images 55), and a picked-up image 55 (fifth (bottommost) picked-up image 55 from the top) showing a frontal view of only one of the plural tumors 56c.

The image string 52 of the region B includes only picked-up images 55 showing a bird's-eye view of one or more tumors 56c.

The image string 52 of the region C includes picked-up images 55 obtained by observing a single tumor 56c from different directions at different enlargement ratios.

Thus, in a stage after observation with the endoscope 10 is finished such as shown in FIG. 4, for example, the region A, in which the second picked-up image 55 from the top shows a bird's-eye view of all the plural tumors 56c, offers an option of selecting and keeping the second picked-up image 55 as a diagnostic image in medical records. Also, the region B offers an option of deleting the bottommost picked-up image 55 in which one of two tumors 56c is lost due to movement or the like of the endoscope 10 in an image pickup direction. Furthermore, the region C in which the picked-up image 55 at the bottom is an enlarged front image, allows tissue properties and condition to be grasped and thus offers an option of selecting and keeping the second picked-up image 55 as a diagnostic image in medical records.

Next, the control unit 24 judges whether or not the sort order has been changed by the user (Step S27). If it is judged that the sort order has been changed, the control unit 24 sets the changed sort order (Step S28), and then goes to Step S26 described above to list the picked-up images 55 in the new sort order. Consequently, the user can change to a desired criterion and observe the picked-up images 55 rearranged based on the changed criterion.

On the other hand, if it is judged in Step S27 that the sort order has not been changed, the control unit 24 judges whether or not to finish the observation (Step S29). When it is judged that the observation is not to be finished, the control unit 24 returns to Step S24 to perform the process described above, but when it is judged that the observation is to be finished, the control unit 24 finishes the process.

Since the first embodiment configured as described above identifies all the image pickup position information at least partially overlapping the specified positions or regions in three-dimensional shape information, acquires all the picked-up images 55 associated with the identified image pickup position information from the image pickup information storage unit 22, and generates an image string by arranging the acquired picked-up images 55 for each position or region based on a predetermined criterion, the user can quickly reach necessary information (such as a picked-up image 55 suitable for determining tissue properties and condition of a tumor 56*c*) among plural images.

Then, since plural positions or regions are specified and display areas, in each of which an image string is displayed are generated, it is easy to select images of a desired object and it is possible to make comparisons among the images at each position or in each region or make comparisons among each position or region easily at a glance.

Also, since information about the image pickup area in three-dimensional shape information is included in the image pickup position information, the image pickup area can be easily grasped visually.

Furthermore, since the predetermined criterion is selectively changeable among plural criteria, the image string can be rearranged in such a way as allow necessary information to be reached most easily.

In so doing, if distance information is used as the predetermined criterion, a magnitude relationship of a shooting distance from the objective optical window 11 to a tumor when the object image is picked up can be grasped promptly.

Also, if a distance from a specific position of an object to a position indicated by the image pickup position information is used as the predetermined criterion, for example, when there are plural tumors, it can be assumed easily which tumors are the same tumors.

Furthermore, if a time series is adopted as the predetermined criterion, images can be checked by remembering procedures and state of affairs of observation with the endoscope 10.

In addition, if size of a predetermined feature site in the predetermined luminal organ is used as the predetermined criterion, a magnitude relationship of tumors or the like can be grasped easily.

Besides, since the specification unit is allowed to specify image pickup position information as a specified position or region, it is easy to specify the image pickup position information and it is possible to see tumors and the like as a group.

In this way, it is possible to look back on an observation situation during observation and thereby determine whether or not any more images needs to be acquired, review images after the observation is finished, and select an appropriate image for carrying out diagnosis from a group of picked-up images 55 of which the image pickup area overlaps at least part of specified regions in the luminal organ.

Second Embodiment

Figure 8:
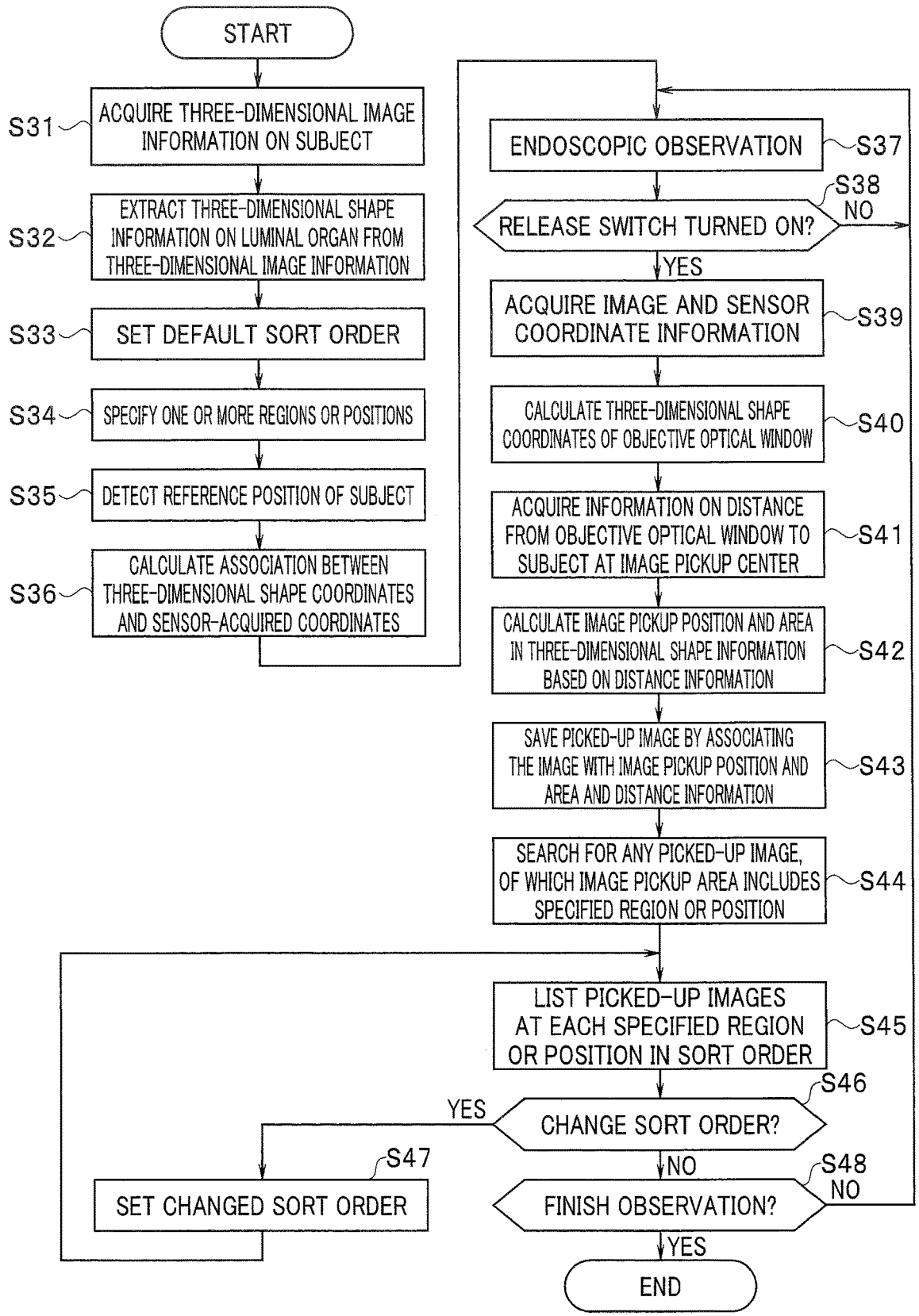
FIG. 8 is a flowchart showing a process of observing an object when a predetermined luminal organ is a renal pelvis and renal calyxes in a second embodiment of the present invention.

FIGS. 8 to 11 show a second embodiment of the present invention, where FIG. 8 is a flowchart showing a process of observing an object when the predetermined luminal organ is a renal pelvis and renal calyxes.

In the second embodiment, parts similar to those of the first embodiment described above are denoted by the same reference numerals as the corresponding parts, and description thereof will be omitted as appropriate, and mainly differences from the first embodiment will only be described.

Whereas the bladder 56 has been taken as an example of the predetermined luminal organ in the first embodiment described above, the renal pelvis and renal calyxes are taken as an example in the present embodiment.

Once the process is started, three-dimensional image information on the subject is acquired from the three-dimensional shape information storage unit 23 (Step S31). That is, whereas three-dimensional model images of a luminal organ are assumed to be three-dimensional shape information in the first embodiment described above, three-dimensional image information on the luminal organ acquired from the subject himself/herself is assumed in the present embodiment.

Here, the three-dimensional image information on the subject is acquired beforehand, from the subject himself/herself, for example, by a CT apparatus or an MRI apparatus. The three-dimensional image information acquired in this way is managed, for example, by an in-hospital workstation. Thus, although FIG. 1 has shown an example in which the three-dimensional shape information storage unit 23 is provided in the image processing apparatus 20, the three-dimensional shape information storage unit 23 may be, for example, an in-hospital workstation or the like provided outside the image processing apparatus 20.

Next, the control unit 24 extracts and reads three-dimensional shape information on the predetermined luminal organ, which is, for example, a renal pelvis and renal calyxes in this case (in FIGS. 9 to 11, the renal pelvis and renal calyxes are denoted collectively by reference numeral 57), from the three-dimensional image information on the subject acquired and stored in the three-dimensional shape information storage unit 23 (Step S32). When the three-dimensional shape information storage unit 23 is, for example, an in-hospital workstation, the reading is done as a data download, and the read three-dimensional shape information is processed by the image processing unit 21 under the control of the control unit 24 and then displayed on the monitor 50, for example, as a map 51 such as shown in FIG. 9.

Note that although it has been stated that the three-dimensional image information on the subject is acquired beforehand by a CT apparatus or the like, a method for acquiring the three-dimensional image information is not limited to this. For example, the image processing unit 21 may be designed to generate three-dimensional image information corresponding to the picked-up image picked up (observed) by the image pickup unit 12 of the endoscope 10 using an observation position and line-of-sight direction data which are based on the picked-up image picked up by the image pickup unit 12.

In this case, the image processing unit 21 may estimate a corresponding three-dimensional shape from a single two-dimensional image as with, for example, the method described in Japanese Patent No. 5354494 or another publicly known method such as a shape-from-shading (SFS) technique. Techniques available for use also include a stereo technique which uses two or more images, a technique for estimating a three-dimensional shape based on monocular ambulatory vision, a SLAM technique, and a technique for estimating a three-dimensional shape in combination with a position sensor. Also, in estimating a three-dimensional shape, three-dimensional shape data may be built with reference to three-dimensional image data acquired from a tomogram acquisition apparatus such as an external CT apparatus.

Figure 9:
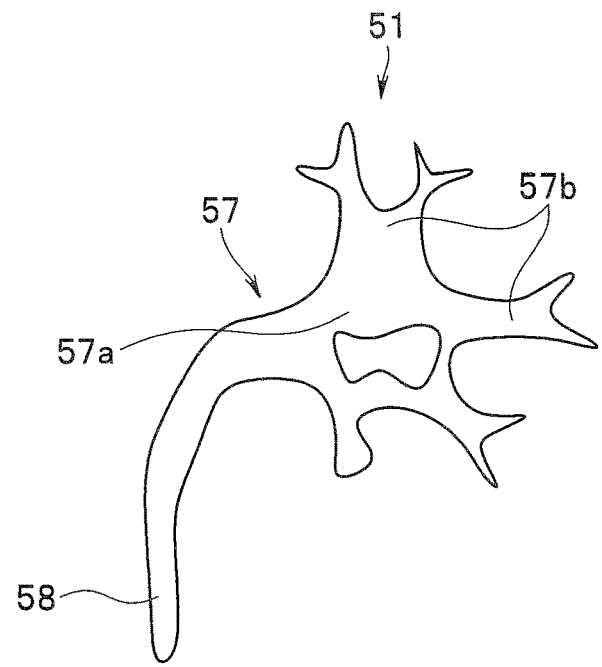
FIG. 9 is a diagram showing a display example of a map presented before a position or region is specified in a medical equipment system according to the second embodiment.

Here, FIG. 9 is a diagram showing a display example of a map 51 presented before a position or region is specified in the medical equipment system.

As illustrated, a map 51 of the predetermined luminal organ created from the three-dimensional shape information (a two-dimensional map of a renal pelvis and renal calyxes 57, in this case) is displayed on the monitor 50 and a renal pelvis 57a, renal calyxes 57b, and a ureter 58 are displayed on the map 51.

Then, a default sort order (list order) for an image string 52 is set as with the first embodiment described above (Step S33).

Subsequently, the control unit 24 waits until one or more positions or regions from which the user wants to display a picked-up image 55 is specified on the map 51 shown in FIG. 9 (Step S34). Then, when a position or region is specified, the specified position or region is displayed by being superimposed on the map 51 displayed on the monitor 50.

Figure 10:
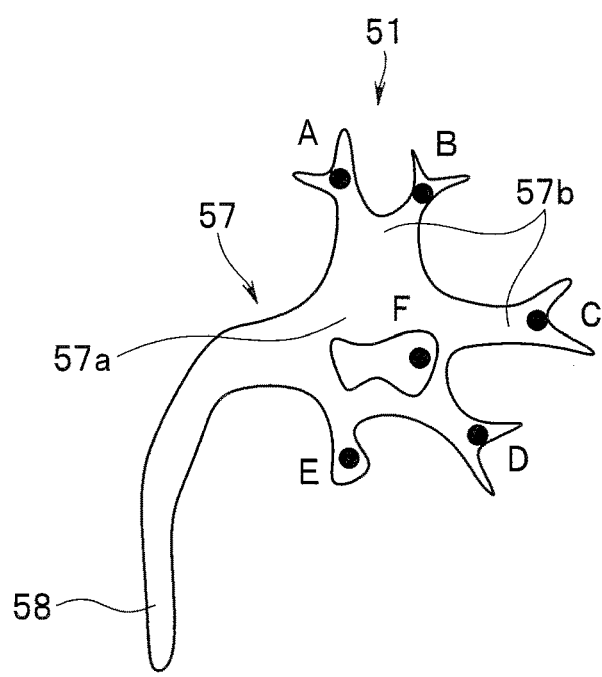
FIG. 10 is a diagram showing an example of a map displayed after a position or region is specified in the medical equipment system according to the second embodiment.

FIG. 10 is a diagram showing an example of the map 51 displayed after a position or region is specified in the medical equipment system. In the example shown in FIG. 10, six positions A to F are specified, but regions may be specified alternatively. Note that the positions or regions may be specified by the user with other timing.

Next, the insertion portion of the endoscope 10 is inserted into the subject, and with the distal end of the insertion portion placed in contact with a reference position of the subject, i.e., with a predetermined reference position in the renal pelvis and renal calyxes 57 in this case, position detection is done using the magnetic sensor 13 (Step S35).

Then, the association between the position information detected by the magnetic sensor 13 (sensor coordinate information) and coordinates (three-dimensional shape coordinates) in the three-dimensional shape information is calculated by the alignment unit 26 (Step S36). Note that the sensor coordinate information and three-dimensional shape coordinates may be associated with each other using another appropriate technique as with the first embodiment described above.

Then, observations in the luminal organ are carried out with the endoscope 10 (Step S37) and the control unit 24 judges whether or not the release switch is turned on (Step S38).

If it is judged here that the release switch is not turned on, the control unit 24 returns to Step S37 to continue the endoscopic observation.

On the other hand, if it is judged in Step S38 that the release switch is turned on, the image pickup unit 12 acquires the picked-up image 55 and acquires sensor coordinate information at a time point when the release switch is turned on from the magnetic sensor 13 (Step S39).

Then, based on the acquired sensor coordinate information, the alignment unit 26 calculates the three-dimensional shape coordinates of the objective optical window 11 (Step S40).

Also, the distance information acquisition unit 25 acquires distance information on a distance from the objective optical window 11 to, for example, a center of the image pickup area in the subject when the release switch is turned on (Step S41).

Based on the three-dimensional shape coordinates of the objective optical window 11 calculated in Step S40, the distance information acquired in Step S41, and angle-of-view information on the endoscope 10, at least one of (e.g., both, in this case) the image pickup area in the three-dimensional shape information on the picked-up image 55 acquired in Step S39 and an image pickup position, which is, for example, a center of the image pickup area is calculated (Step S42).

Note that although in Steps S41 and S42, the image pickup area and image pickup position are calculated by calculating distance, an intersection between a field-of-view area or a centerline of field of view and three-dimensional image information may be calculated as the image pickup area or image pickup position by finding the three-dimensional shape coordinates of the field-of-view area or centerline of field of view from the three-dimensional shape coordinates of the objective optical window and angle-of-view information on the endoscope 10 without calculating the distance.

Then, the picked-up image 55 subjected to image processing by the image processing unit 21, the image pickup position and image pickup area calculated by the image pickup position calculation unit 27, and the distance information acquired by the distance information acquisition unit 25, are saved in the image pickup information storage unit 22 by being associated with one another (Step S43).

The control unit 24 searches the picked-up images 55 stored in the image pickup information storage unit 22 for the picked-up image 55, at least a partial image pickup area of which overlaps the position(s) or region(s) specified in Step S34 (Step S44).

Then, the control unit 24 presents a display as shown in FIG. 11 (Step S45). FIG. 11 is a diagram showing an example in which picked-up images 55 for each specified position or region are displayed together with a map 51 on the monitor 50 in the medical equipment system.

As illustrated, a map 51 of the predetermined luminal organ created from the three-dimensional shape information (the renal pelvis and renal calyxes 57, in this case) and an image string 52 are displayed, for example, next to each other on left and right on the monitor 50.

Here, specified positions A to F are displayed on the map 51 shown in FIG. 11 as with the map 51 shown in FIG. 10.

Also, the picked-up images 55 which include the respective specified positions in the image pickup area are acquired from the image pickup information storage unit 22 for each of the specified positions A to F, arranged in sort order based on the predetermined criterion described above, and listed in the image string 52.

Regarding the predetermined criterion, when the renal pelvis and renal calyxes 57 are used as with the present embodiment, other than the examples described above, size of a hole portion in the renal pelvis and renal calyxes 57 may be adopted as well. In so doing, as information on the size of an object (predetermined feature site) on the picked-up image 55, information on the size of the hole portion is acquired. Note that as the information on the size of the object (predetermined feature site) on the picked-up image 55, information on size of, for example, a minor calyx 57*c* or a calculus may be further acquired, saved in the image pickup information storage unit 22 by being associated with the picked-up images 55, and used as a predetermined criterion in arranging and displaying the images.

The picked-up images 55 show, for example, minor calyxes 57*c*. Also, if there is no image pickup position information overlapping any of plural positions or regions, under the control of the control unit 24, the image processing unit 21 superimposes indicator information 59 indicating that there is no picked-up image 55, on a display area configured to display the image string 52. Here, since there is no picked-up image 55 of which the image pickup area overlaps the specified position D, for example, "No data" is displayed as the indicator information 59 to that effect, allowing the user to grasp easily at a glance that there is no picked-up image 55.

In the example shown in FIG. 11, based on features displayed on the picked-up images 55 at respective positions A to F, the user can make the following determinations and selections.

First, the respective image strings 52 at positions A to C include images showing a bird's-eye view of plural minor calyxes 57*c*.

Also, no picked-up image 55 is acquired at position D.

Furthermore, the image string 52 acquired at position E includes an image of a minor calyx 57*c* picked up at a short distance and an image of the minor calyx 57*c* picked up at a long distance.

Then, the image string 52 at position F includes an image showing a bird's-eye view of plural minor calyxes 57*c* and images observing respective minor calyxes 57*c* at close range.

Thus, during observation with the endoscope 10, the user can determine whether to additionally acquire close-up images of each minor calyx 57*c*, for example, at positions A to C. Also, at position D, the user can determine to acquire images of minor calyxes 57*c* by concluding that there has been a failure to observe minor calyxes 57*c*.

On the other hand, after the observation with the endoscope 10 is finished, regarding, for example, position A, the user has an option of selecting and keeping the second picked-up image 55 from the top, which shows a bird's-eye view of all three minor calyxes 57*c*, as a diagnostic image in medical records. Also, regarding position E, the user has an option of keeping only the image of the minor calyx 57*c* picked up at close range in medical records as a diagnostic image.

Next, the control unit 24 judges whether or not the sort order has been changed by the user (Step S46). If it is judged that the sort order has been changed, the control unit 24 sets the changed sort order (Step S47), and then goes to Step S45 described above and lists the picked-up images 55 in the new sort order. Consequently, the user can change to a desired criterion and observe the picked-up images 55 rearranged based on the changed criterion.

On the other hand, if it is judged in Step S46 that the sort order has not been changed, the control unit 24 judges whether or not to finish the observation (Step S48). When it is judged that the observation is not to be finished, the control unit 24 returns to Step S37 to perform the process described above, but when it is judged that the observation is to be finished, the control unit 24 finishes the process.

As with the first embodiment described above, the second embodiment configured as described above allows the user to look back on an observation situation during observation with the endoscope 10 and thereby judge whether or not it is necessary to further acquire an image or whether or not there has been any failure to observe the renal calyxes or the like; review images after the observation with the endoscope 10 is finished, and select an appropriate image for carrying out diagnosis from among the picked-up images 55 classified for each specified position or region.

Besides, since three-dimensional image information acquired from the subject himself/herself is used as three-dimensional shape information, it is possible to perform alignment more accurately and display a more accurate map 51.

Note that whereas mainly a medical equipment system has been described above, the present invention is also applicable to an operation method configured to operate the medical equipment system as described above, a processing program configured to cause a computer to operate the medical equipment system as described above, a computer-readable, non-temporary recording medium configured to store the processing program, and so on.

Also, the present invention is not limited to the precise embodiments described above and may be embodied by changing components in the implementation stage without departing from the spirit of the invention. Also, various aspects of the invention can be implemented using appropriate combinations of the components disclosed in the above embodiments. For example, some of the components disclosed in the embodiments may be deleted. Furthermore, components may be combined as required across different embodiments. Thus, needless to say, various alterations and applications are possible without departing from the spirit of the invention.

What is claimed is:

1. A medical equipment system comprising:
  a processor comprising hardware, wherein the processor is configured to:
    control a storage to store a picked-up image obtained by picking up an object image of an object in a predetermined luminal organ and image pickup position information indicating an image pickup position or image pickup area of the object picked up in the picked-up image, by associating the picked up image and the image pickup position information with each other,
      wherein the object image is formed by an objective optical window in the predetermined luminal organ, and
      wherein the picked up image is acquired by an image sensor configured to pick up the object image;
    acquire a current picked-up image acquired by the image sensor and current position information on a current position of the objective optical window at a time when the current picked-up image is acquired;
    align the current position information acquired with three-dimensional shape information on the predetermined luminal organ;
    based on the current position information aligned with the three-dimensional shape information, calculate current image pickup position information indicating a current image pickup position or current image pickup area of an object picked up in the current picked-up image in the three-dimensional shape information;
    identify, from the storage, the image pickup position information indicating the image pickup position or image pickup area as at least partially overlapping the current image pickup position or current image pickup area indicated by the current image pickup position information; and control a display to display a display image including the current picked-up image and the picked-up image associated with the image pickup position information identified.

2. The medical equipment system according to claim 1, further comprising:

an endoscope comprising:
the objective optical window; and
the image sensor; and
the storage.

3. The medical equipment system according to claim 1, wherein the processor is configured to, if the image pickup position information indicating the image pickup position or image pickup area is not identified as at least partially overlapping the current image pickup position or current image pickup area indicated by the current image pickup position information, control the display to display indicator information indicating that a picked-up image with the image pickup position or image pickup area at least partially overlapping the current image pickup position or current image pickup area does not exist.

4. The medical equipment system according to claim 1, wherein the processor is configured to control the display to display, as the display image, an image string by arranging the picked-up image associated with the image pickup position information identified and one or more past picked-up images based on a predetermined criterion.

5. The medical equipment system according to claim 4, wherein the processor is configured to select the predetermined criterion from any one of:
a distance from the objective optical window to the predetermined luminal organ;
a distance from a specific position of the object to a position in indicated by the image pickup position information;
a time series; and
a size of a predetermined feature site in the predetermined luminal organ.

6. An operation method comprising:
controlling a storage to store a picked-up image obtained by picking up an object image of an object in a predetermined luminal organ and image pickup position information indicating an image pickup position or image pickup area of the object picked up in the picked-up image, by associating the picked up image and the image pickup position information with each other,
wherein the object image is formed by an objective optical window in the predetermined luminal organ, and
wherein the picked up image is acquired by an image sensor configured to pick up the object image;
acquiring a current picked-up image acquired by the image sensor and current position information on a current position of the objective optical window at a time when the current picked-up image is acquired;
aligning the current position information acquired with three-dimensional shape information on the predetermined luminal organ;
based on the current position information aligned with the three-dimensional shape information, calculating current image pickup position information indicating a current image pickup position or current image pickup area of an object picked up in the current picked-up image in the three-dimensional shape information;
identifying, from the storage, the image pickup position information indicating the image pickup position or image pickup area as at least partially overlapping the current image pickup position or current image pickup area indicated by the current image pickup position information; and
controlling a display to display a display image including the current picked-up image and the picked-up image associated with the image pickup position information identified.

7. A computer-readable storage device storing a program that causes a computer to at least perform:
controlling a storage to store a picked-up image obtained by picking up an object image of an object in a predetermined luminal organ and image pickup position information indicating an image pickup position or image pickup area of the object picked up in the picked-up image, by associating the picked up image and the image pickup position information with each other,
wherein the object image is formed by an objective optical window in the predetermined luminal organ, and
wherein the picked up image is acquired by an image sensor configured to pick up the object image;
acquiring a current picked-up image acquired by the image sensor and current position information on a current position of the objective optical window at a time when the current picked-up image is acquired;
aligning the current position information acquired with three-dimensional shape information on the predetermined luminal organ;
based on the current position information aligned with the three-dimensional shape information, calculating current image pickup position information indicating a current image pickup position or current image pickup area of an object picked up in the current picked-up image in the three-dimensional shape information;
identifying, from the storage, the image pickup position information indicating the image pickup position or image pickup area as at least partially overlapping the current image pickup position or current image pickup area indicated by the current image pickup position information; and
controlling a display to display a display image including the current picked-up image and the picked-up image associated with the image pickup position information identified.

* * * * *